United States Patent [19]
Akiba et al.

[11] Patent Number: 4,999,289
[45] Date of Patent: Mar. 12, 1991

[54] LIPASE, ITS PRODUCTION AND USE FOR ASSAY OF TRIGLYCERIDES

[75] Inventors: Tetsunori Akiba, Kani; Shotaro Yamaguchi; Satoru Suzuki, both of Aichi; Kimiyasu Isobe, Konan; Kuniyoshi Matsunaga, Ichinomiya, all of Japan

[73] Assignee: Amano Pharmaceutical Co. Ltd.,, Aichi, Japan

[21] Appl. No.: 34,452

[22] Filed: Apr. 6, 1987

[30] Foreign Application Priority Data

Apr. 10, 1986 [JP] Japan .............................. 61-082991
Apr. 10, 1986 [JP] Japan .............................. 61-082992

[51] Int. Cl.$^5$ .......................... C12Q 1/44; C12N 9/20
[52] U.S. Cl. ...................................... 435/19; 435/198; 435/188; 435/933; 435/254
[58] Field of Search ................ 435/19, 198, 189, 184, 435/933, 253, 254

[56] References Cited

FOREIGN PATENT DOCUMENTS 149520   7/1985  European Pat. Off. ............ 435/198
62-000287 6/1987  Japan ................................. 435/933
60-188072 9/1988  Japan ................................. 435/198

OTHER PUBLICATIONS

Okumura et al., J. Biochem, vol. 87, pp. 205-211 Ry (1980).
Sigma Catalog 1987, pp. 316,1365.

Primary Examiner—Esther L. Kepplinger
Assistant Examiner—Toni R. Scheiner
Attorney, Agent, or Firm—Wegner, Cantor, Mueller & Player

[57] ABSTRACT

Lipase isolated from Penicillium characterized by the following properties:
(1) Efficiently hydrolyzes triglycerides of fatty acids having 4–18 carbon atoms;
(2) Hydrolysis of such triglycerides with such lipase produces at least 5 moles of glycerol per 100 moles of fatty acid;
(3) Optimal pH range for said hydrolysis 5-7;
(4) Stable in the pH range of 4.5-6;
(5) Optimal temperature range for activity 35°-40° C.;
(6) thermal stability up to about 35° C.;
(7) Activated by surface-active agents, but not substantially inhibited by such surface-active agents in concentration up to 5%;
(8) Molecular weight about 1000,000 to 120,000;
(9) Isoelectric point about pH 3.84.

9 Claims, 9 Drawing Sheets

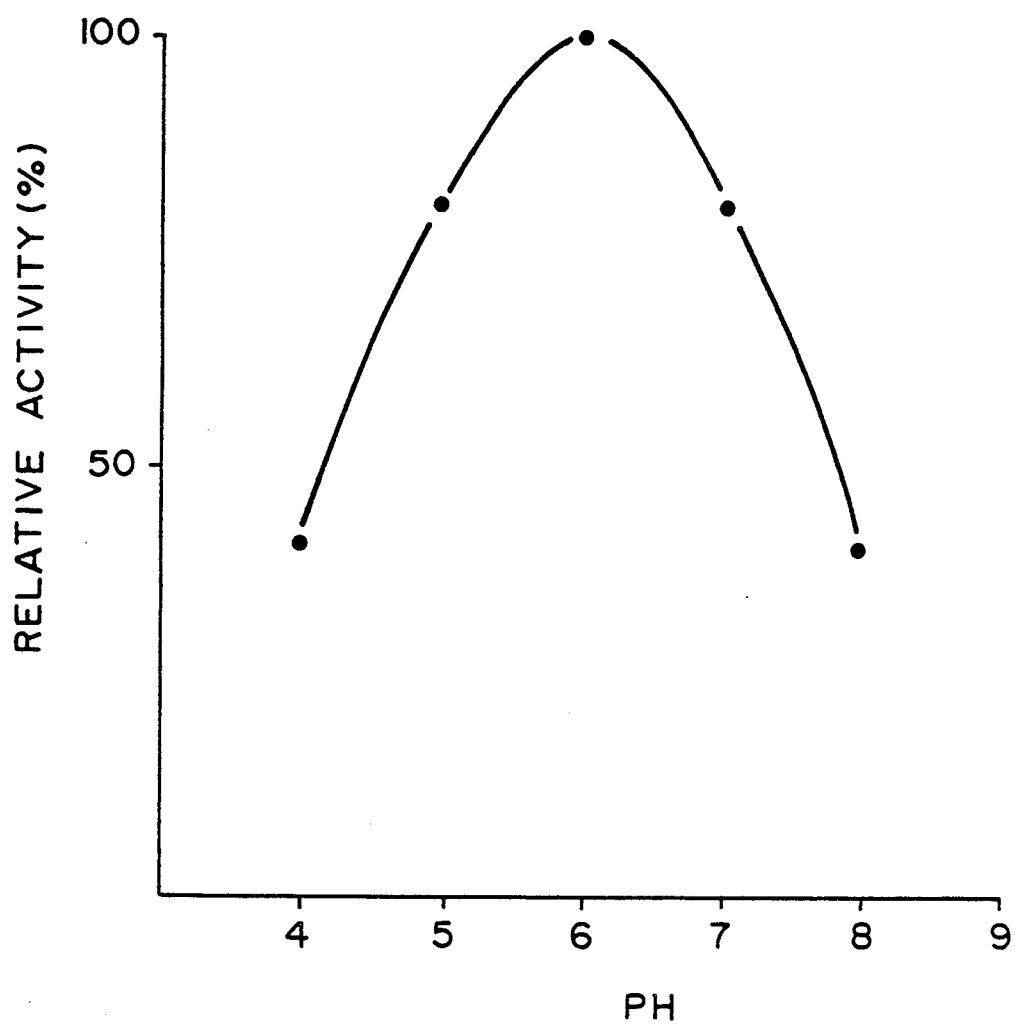
F I G. 1

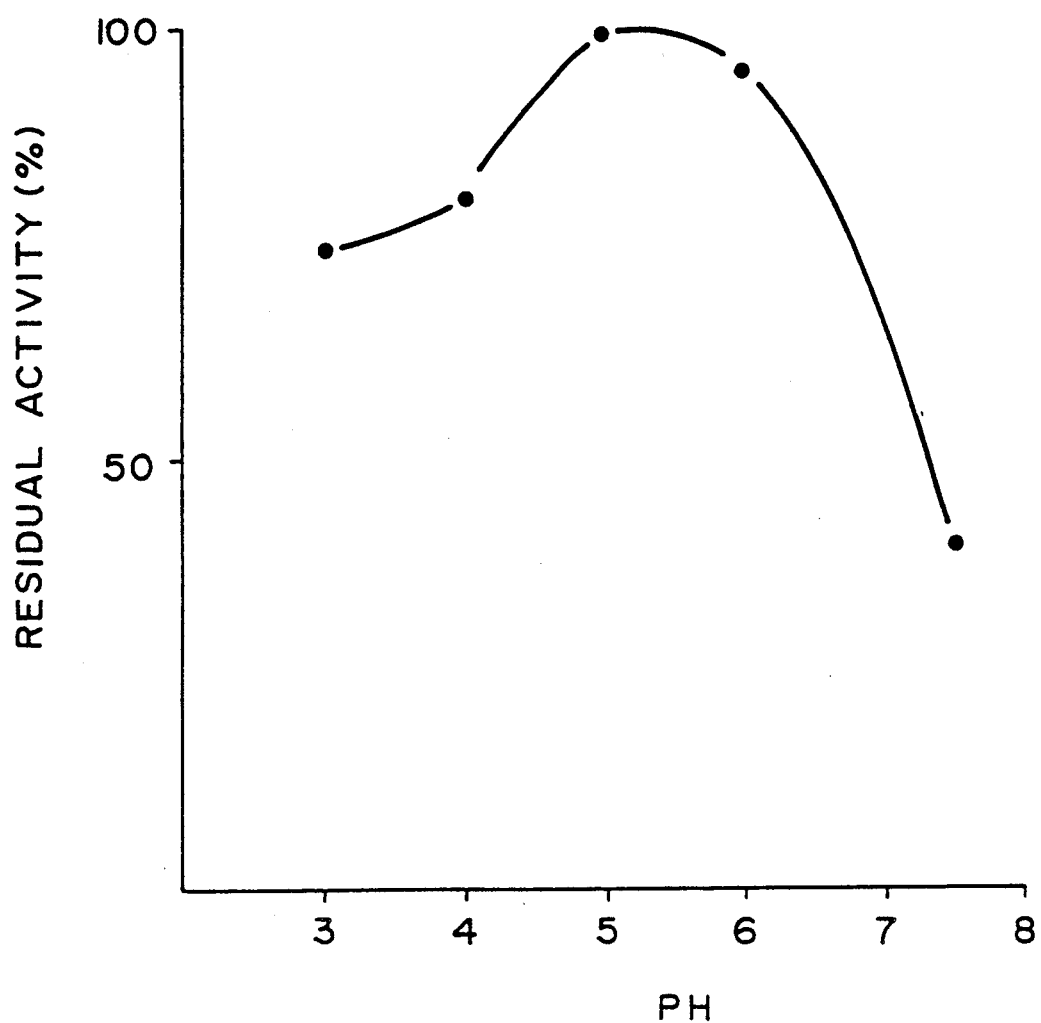
F I G. 2

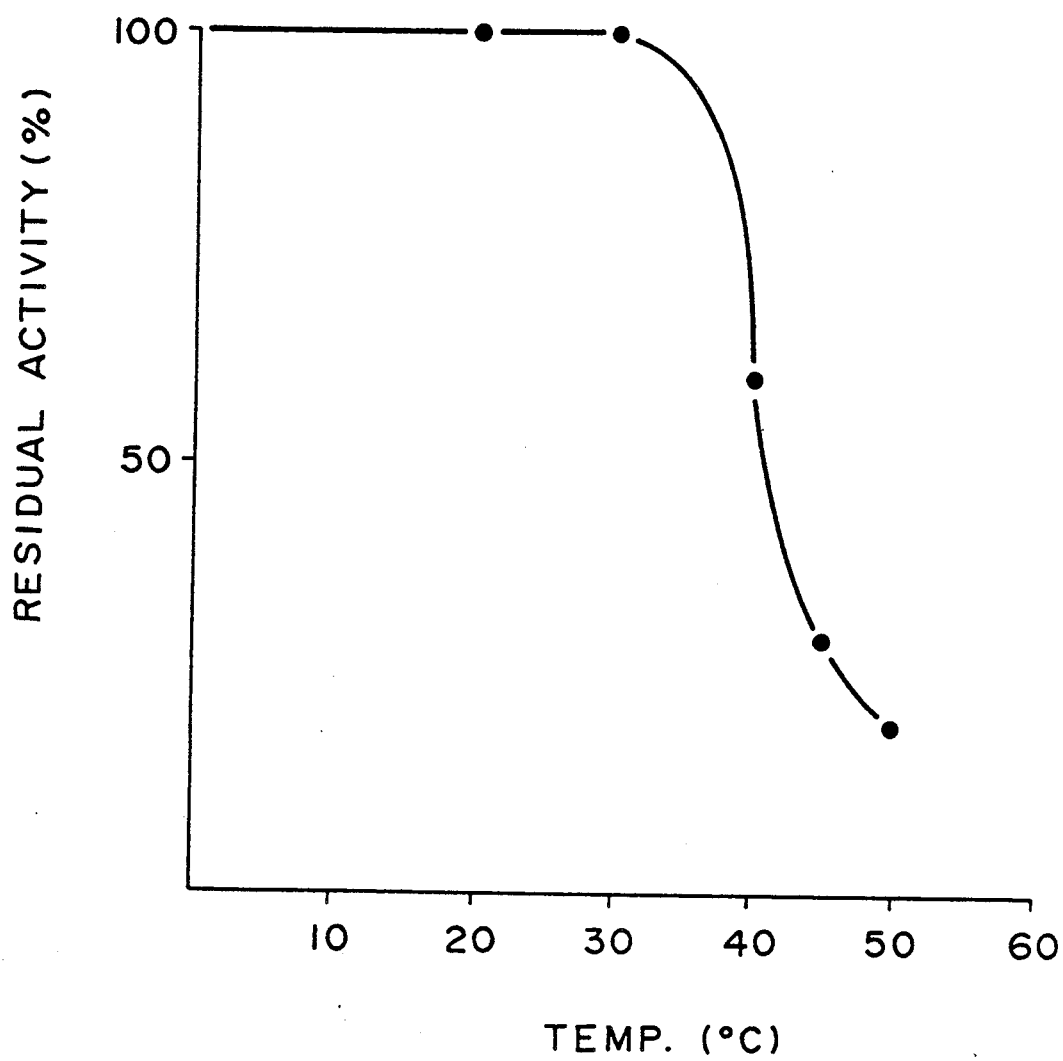
F I G. 4

LIPASE, ITS PRODUCTION AND USE FOR ASSAY OF TRIGLYCERIDES

BACKGROUND OF THE INVENTION

1. Field of the Invention

The present invention relates to a novel lipase, its production, and a method of hydrolyzing triglycerides by use of this novel lipase. The lipase of the present invention is used for hydrolyzing triglycerides and particularly, triglycerides present in serum. More particularly, the present invention relates to a method of hydrolyzing triglycerides by action of a lipase originating from the genus Penicillium on triglycerides contained in a biological body fluid sample such as serum. The method of the present invention is used for an assay of triglycerides present in a serum or the like.

2. Related Background Art

Methods have been known for an assay of triglycerides by hydrolyzing triglycerides present in a biological body fluid sample such as serum to determine a liberated fatty acid or glycerol, but almost all of the methods having been put into practical use are those for determining glycerol. Liberated glycerol is assayed after being further converted to detectable products by the action of glycerol kinase, glycerol dehydrogenase or glycerol oxidase.

The lipase first used for hydrolyzing triglycerides in serums was a lipase originating from pancreas of animals. However, this enzyme was not capable of perfectly hydrolyzing triglycerides. In order to perfectly hydrolyze triglycerides in serums, studies have been made searching for lipases derived from microorganisms, on the hydrolysis by a combination of lipases having different properties, and on the hydrolysis by a combination of a lipase with chemicals. For example, known are a lipase from *Rhizopus arrhizus* (Japanese Patent Publication No. 15638/1984 and Japanese Unexamined Patent Publication No. 25693/1977), a lipase from the genus Pseudomonas (Japanese Unexamined Patent Publications No. 50990/1974, No. 69186/1974, No. 89596/1974, No. 113695/1974, and No. 58898/1982), combined use of a lipase and a protease (Japanese Patent Publication No. 9518/1979 and Japanese Unexamined Patent Publication No. 114493/1978), a combination comprising a lipase from *Rhizopus arrhizus*, a carboxylesterase originating from pork liver, and an alkyl sulfate of an alkali metal or alkaline earth metal (Japanese Unexamined Patent Publication No. 64495/1974), a combination comprising a lipase from the genus Candida, a pancreas lipase, and a bile salt (Japanese Unexamined Patent Publication No. 11987/1977), a lipase from the genus Chromobacterium (Japanese Unexamined Patent Publications No. 68297/1976, No. 74692/1976 and No. 58898/1982), a combination comprising a lipase from *Rhizopus arrhizus* and a lipase from *C. cylindracea* (Japanese Unexamined Patent Publication No. 25694/1977 and Japanese Patent Publication No. 29/1981), a combination comprising a lipase from *C. rugosa* and a surface-active agent (Japanese Patent Publication No. 39158/1982), a combination comprising a lipase from *Rhizopus arrhizus* and a lipase from *P. fluorescens* (Japanese Patent Publication No. 28276/1982), a combination comprising a lipase from the genus Rhizopus or the like and a cholesterol esterase (Japanese Patent Publication No. 46799/1981), and a combination comprising a lipase and a surface-active agent, a phenol derivative or an aniline derivative (Japanese Patent Publication No. 5677/1983).

It is also known that a certain kind of lipases produced by the genus Pseudomonas yield about 2 moles of glycerol per 100 moles of fatty acid (Japanese Unexamined Patent Publication No. 187780/1984).

The present inventors do not know any report that a lipase originating from the genus Penicillium is effective for hydrolyzing serum triglycerides, but it is known that the genus Penicillium produces a lipase. Iwai et al report that a strain of *Penicillium cyclopium Westring* produces two kinds of lipases (Agr. Biol. Chem., Vol. 39, pp.1063-1070, 1975). They also report that a strain of *Penicillium cyclopium* M1 produces two kinds of lipases (J. Biochem., Vol. 87, pp. 205-211, 1980).

In the above prior art relating to the hydrolysis of triglycerides present in serum, the lipase originating from microorganisms when used alone, has been still unable to sufficiently hydrolyze triglycerides or has produced a slow rate of hydrolysis. In another aspect, there has been a drawback that the activities of these lipases may be inhibited by a surface-active agent contained in a reagent composition used for an assay of triglycerides. Also, the production thereof has been cumbersome when a plurality of lipases originating from different sources is used in combination.

SUMMARY OF THE INVENTION

An object of the present invention is to provide a novel lipase that can solve these problems, can sufficiently hydrolyze triglycerides even when used alone, and can be substantially free from any inhibition of its activities due to surface-active agents used for emulsification of fats in an assay of triglycerides, for example, surface-active agents of polyethylene glycol alkyl phenyl ether type, a process for producing the same; and a method of hydrolyzing triglycerides by using such a novel lipase.

According to one aspect of the present invention, there is provided a lipase having the properties of acting effectively triglycerides so as to produce 5 moles or more of glycerol per 100 moles of fatty acid, and when activated by a surface-active agent, being substantially free from inhibition of activities within the concentration range of 5% or less of the surface-active agent.

According to another aspect of the present invention, there is provided a process for producing a lipase, which comprises cultivating a strain belonging to the genus Penicillium and capable of producing a lipase having the properties of hydrolyzing triglycerides so as to produce 5 moles or more of glycerol per 100 moles of fatty acid, and when activated by a surface-active agent, being substantially free from inhibition of activities within the concentration range of 5% or less of the surface-active agent; and collecting said lipase from the resulting culture.

According to still another aspect of the present invention, there is provided a method of assaying triglyceride, which comprises allowing to act on triglyceride a lipase originating from the genus Penicillium having the properties of acting sufficiently on triglyceride present in a biological body fluid sample to produce 5 moles or more of glycerol per 100 moles of fatty acid formed, and when activated by a surface-active agent, being substantially free from inhibition of activities within the concentration range of 5% or less of the surface-active agent.

BRIEF DESCRIPTION OF THE DRAWING

FIG. 1 is a graph showing an optimum pH range for activity of the lipase of the present invention and, similarly, FIGS. 2, 3, and 4 are graphs showing a stable pH range, a suitable acting temperature range, and thermal stability thereof, respectively;

DESCRIPTION OF THE PREFERRED EMBODIMENTS

Figure 3:
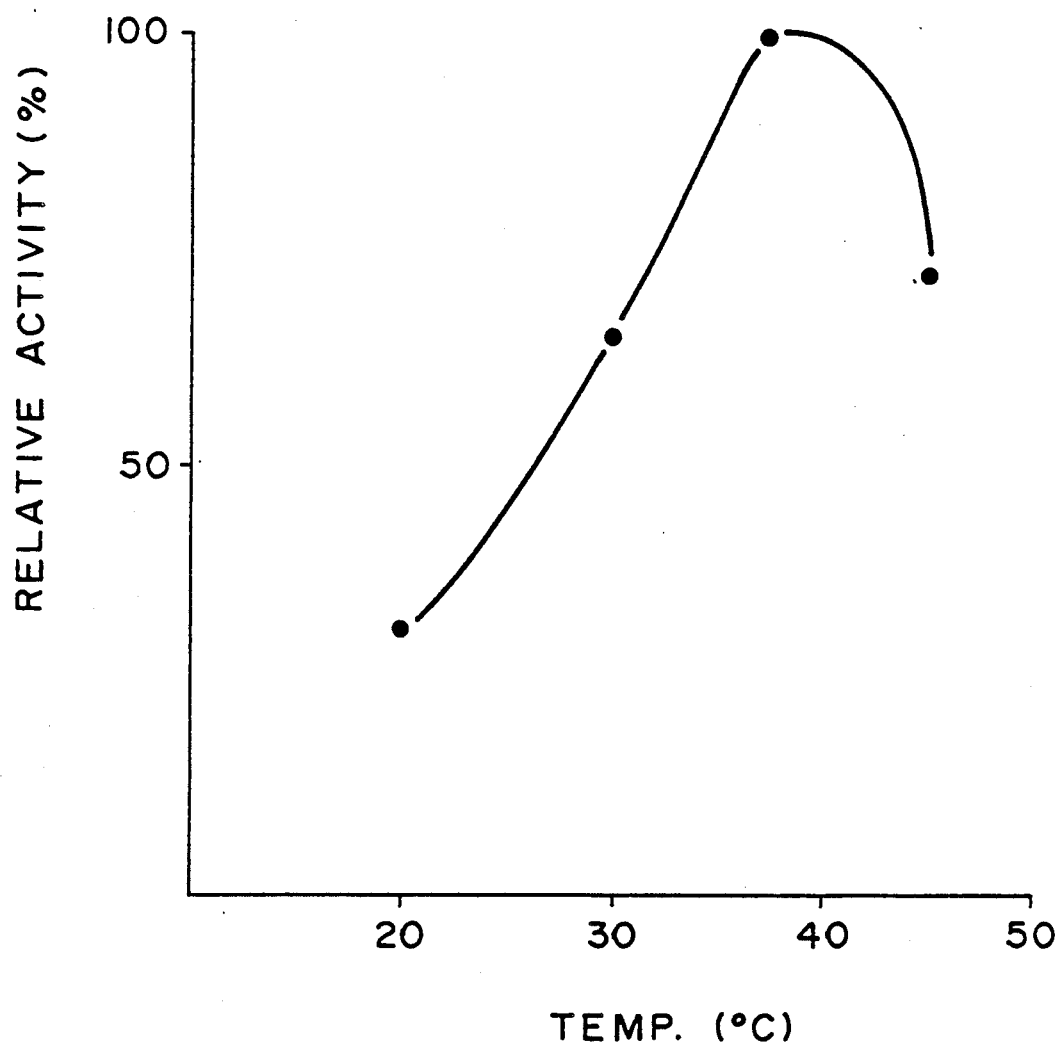

The lipase of the present invention can be obtained by cultivating a strain belonging to the genus Penicillium. The strain of the genus Penicillium may particularly preferably include *Penicillium cyclopium* (ATCC 34613).

*Penicillium cyclopium* (ATCC 34613) has been confirmed to produce at least three kinds of lipases having different properties. The lipase of the present invention is a novel lipase which is one of them and clearly different from the known two kinds mentioned before. This lipase has the following physicochemical properties:

(1) Action:

It hydrolyzes triglycerides yielding at least 5 moles of glycerol per 100 moles of fatty acid.

(2) Substrate specificity:

It can efficiently hydrolyze triglycerides of fatty acids having 4 to 18 carbon atoms.

(3) Optimum pH range for activity: pH 5 to 7.

(4) Stable pH range:

Residual activity was assayed after treatment for 30 minutes at pH 3 to 8 to reveal that the lipase was stable in the pH range of about 4.5 to 6.

(5) Optimum temperature range for activity: 35° to 40° C.

(6) Thermal stability:

Residual activity was assayed after treatment for 30 minutes at pH 7.0 and at temperature of 0° to 50° C. each to reveal that the lipase was stable at temperature up to about 35° C.

(7) Inhibition, activation, and stabilization:

It is activated by a surface-active agent, and the activity was substantially not inhibited within the concentration range of at least 5% or less of the surface-active agent.

(8) Molecular weight: 100,000–120,000 (according to a gel filtration method using Sephadex G-100).

(9) Isoelectric point: pH 3.84 (according to isoelectric electrophoresis using Ampholytes).

(10) Crystal form: Diamond-shaped, plate-like.

The reactivity of the lipase of the present invention, originating from the genus Penicillium, to triglycerides, and that of a known lipase originating from the genus Pseudomonas (trademark: Lipoprotein Lipase-Type A; produced by Toyobo Co., Ltd.) and a known lipase originating from the genus Chromobacterium (produced by Toyo Jozo Co., Ltd.) are contrastingly shown in Table 1.

TABLE 1

| Triglycerides | Penicillium (%) | Pseudomonas (%) | Chromobacterium (%) |
|---|---|---|---|
| Triolein | 100 | 100 | 100 |
| Tripalmitin | 28 | 2 | 22 |
| Trimyristin | 8 | 7 | 53 |
| Trilaurin | 21 | 4 | 103 |
| Tricaprin | 72 | 17 | 166 |
| Tricaprylin | 102 | 64 | 312 |
| Tricaproin | 19 | 2 | 156 |
| Tributylin | 19 | 2 | 94 |

The lipase of the present invention, originating from the genus Penicillium, is also different from the above known lipases in the sensitivity to a surface-active agent and the rate of the formation of fatty acids and glycerol. Namely, the lipase of the present invention is substantially free from inhibition of activities even when the surface-active agent is present in concentration as high as about 5%. This property is very useful for a lipase to hydrolyze triglycerides in serum.

In the present invention, the cultivation of the strain of the genus Pseudomonas may be carried out according to conventional methods generally available for the cultivation of a mold. For example, as a culture medium, a synthetic culture medium or natural culture medium containing a carbon source, a nitrogen source, an inorganic substance, and so forth may be used. The carbon source to be used may include glucose, fructose, maltose, sucrose, molasses, starch, dextrin, organic acids, glycerol, etc. The nitrogen source to be used may include organic nitrogen sources such as malt extract, peptone, yeast extract, dry yeast, meat extract, corn steep liquor, casein, and amino acids, and inorganic nitrogen sources such as nitrates and ammonium salts. The inorganic substance that can be optionally used may include salts of potassium, sodium, magnesium, calcium, zinc, iron, and the like. In order to suppress foaming during cultivation, it is also possible to add an antifoaming agent such as a surface-active agent, silicone, and a vegetable oil.

In general, the cultivation is desirably carried out under aerobic conditions with shaking or aerated stirring. Any conditions may be selected for cultivation conditions such as cultivation temperature and pH of a culture medium if they are in the range where molds can grow to produce a lipase.

Collection of the lipase of the present invention from the culture obtained as above can be carried out by suitably combining known purification methods while utilizing the physicochemical properties thereof. For example, a culture may be filtered or centrifuged to remove cells, followed by purification according to known methods such as salting-out by use of ammonium sulfate, sodium sulfate, etc., precipitation with an organic solvent such as ethanol, methanol, acetone, etc., adsorption chromatography with active carbon, silica gel, alumina, hydroxy apatite, cellulose, etc., ion exchange chromatography with ion exchange resin, ion exchange cellulose, ion exchange Sephadex, etc., gel filtration with Sephadex, Bio-gel, etc., and electrophoresis, ultrafiltration, dialysis, etc. which may be combined or repeated in the order arbitrarily selected.

To hydrolyze triglycerides according to the present invention, the above lipase originating from the genus Penicillium and a biological body fluid sample such as serum are mixed and incubated at an appropriate temperature. It is preferable to add a surface-active agent to the reaction mixture. The surface-active agent may be exemplified by nonionic surface-active agents of polyethylene glycol alkylphenyl ether type, nonylphenol ethoxylate type, or secondary alcohol straight chain ethoxylate type. The surface-active agent may be added in the concentration by which the lipase can be sufficiently activated, and usually of 0.01 to 5%. The lipase may be used in an amount of 0.1 unit to 5 units in terms of glycerol formation activity per 1 ml of a sample. Incubation temperature may preferably range from 20° to 40° C. and the reaction mixture may have the pH of 6 to 8.

When the method of the present invention is used for the assay of triglycerides, the triglyceride can be determined by assaying glycerol liberated from the triglyceride. A known method can be used for the assay of glycerol.

In the present invention, the lipase activity was indicated by using as one unit the amount by which one micro mole equivalent of glycerol was formed in 1 minute when the lipase acted on a substrate olive oil emulsified solution at 37° C.

Assay of Enzymatic Activity (1) Glycerol formation activity:

Glycerol formed is assayed according to an enzymatic method by use of an olive oil emulsified solution as a substrate.

(1) Reagent:

(a) Substrate: 10 g of olive oil (produced by Nakarai Kagaku K.K.), 10 g of Triton X-100, and 30 ml of purified water are stirred for emulsification for 30 minutes by use of a stirrer. Subsequently, added thereto is 20 ml of a 50 mM phosphate buffer solution (pH 6.5) containing 10% bovine serum albumin (Fraction V).

(b) Reagent for assay of glycerol: The following reagents are dissolved in 100 ml of MES [2-(N-morpholino) ethane-sulfonic acid] buffer solution (pH 6.5).

| Triton X-100 | 0.1 g |
| N-Ethyl-N-(2-hydroxy-3-sulfopropyl)-m-toluidine | 64.6 mg |
| 4-Aminoantipyrine | 10.2 mg |
| Disodium EDTA | 37.2 mg |
| Disodium adenosine phosphate | 200 mg |
| Magnesium chloride hexahydrate | 40.7 mg |
| Glycerol kinase | 50 units |
| L-α-Glycerophosphate oxidase | 400 units |
| Peroxidase | 200 units |

(2) Procedure:

A substrate in amount of 1 ml is introduced in a test tube, which is then preheated at 37° C., and 0.1 ml of a diluted enzyme solution is added to initiate the reaction. After reacting at 37° C. for 15 minutes, 2.0 ml of a 0.2 M trichloroacetic acid solution is added to quench the reaction. The quenched solution is filtered with Toyo Filter Paper (No. 131). The filtrate in amount of 0.02 ml is added to 3 ml of the reagent for assay of glycerol, and the mixture is heated to 37° C. for 10 minutes to measure the absorbance at 555 nm.

(3) Indication of activity:

The enzyme amount with which 1 micro mole of glycerol is produced in 1 minute is assumed as 1 unit.

(2) Fatty acid formation activity:

Using an olive oil emulsified solution as a substrate, fatty acids formed are determined by titration with a sodium hydroxide solution.

(1) Procedure:

The above substrate in amount of 1.0 ml is introduced in a test tube, which is then preheated at 37° C., and 0.1 ml of a diluted enzyme solution is added to initiate the reaction. After reacting at 37° C. for 15 minutes, 2.5 ml of an ethanol/acetone mixed solution (1:1) was added to quench the reaction. Several droplets of phenolphthalein is added as an indicator to carry out titration using 1/20 M sodium hydroxide.

(2) Indication of activity:

The enzyme amount with which 1 micro mole of fatty acid is produced in 1 minute is assumed as 1 unit.

EXAMPLE 1

Figure 5:
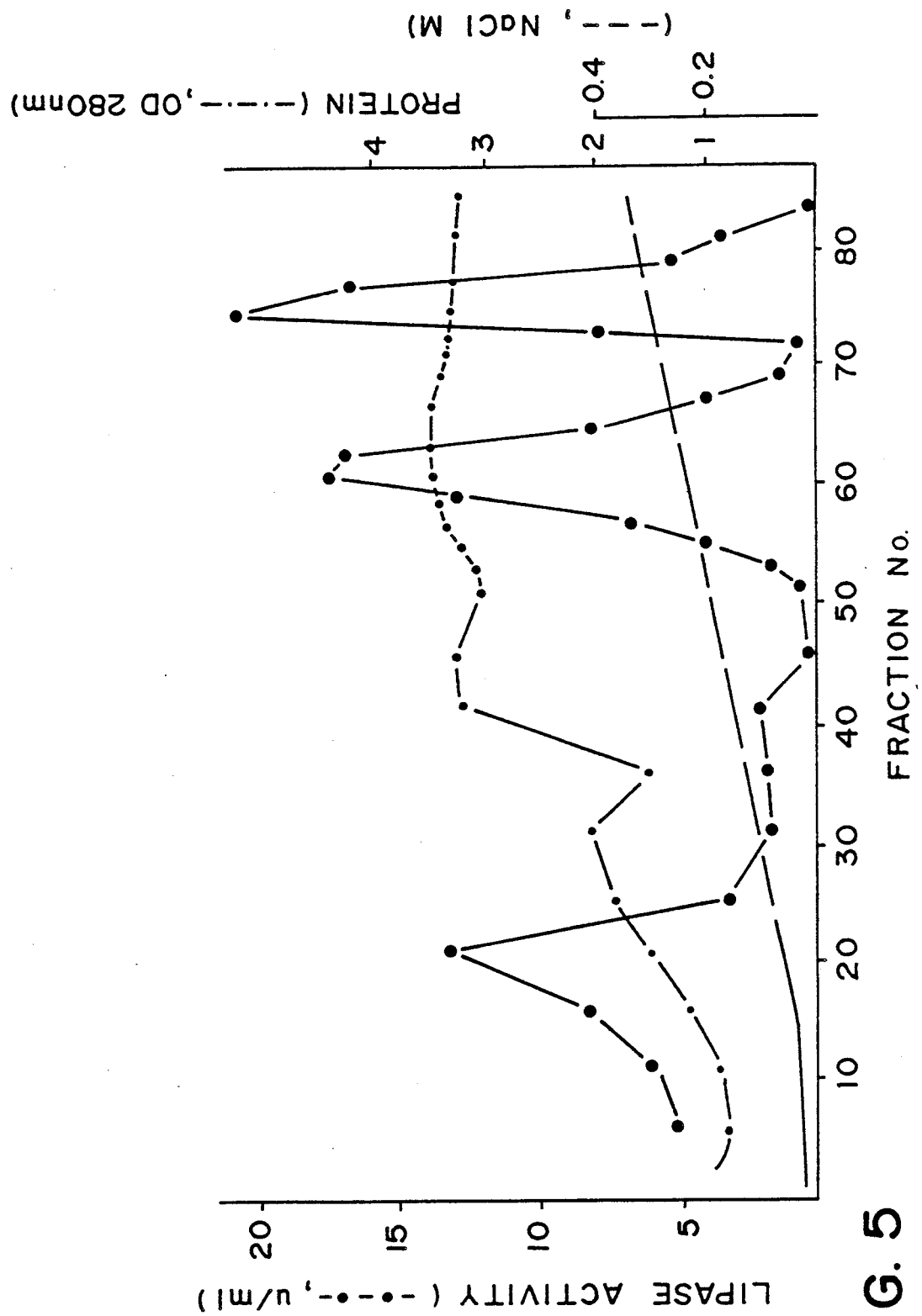
FIG. 5 is a graph showing patterns of column chromatography on DEAE-Sepharose, of three kinds of lipases which *Penicillium cyclopium* (ATCC 34613) produces.

A jar fermenter containing a culture medium comprising 2% of rice bran and 1.5% of corn steep liquor was inoculated with Penicillium cyclopium (ATCC 34613), and the culture was grown at 25° C. for 24 hours to make a seed culture solution. A fermenter containing 500 ml of a culture medium having the same composition as the above was inoculated with the above seed culture solution, and grown at 25° C. for 40 hours. The resulting culture broth was filtered to remove cells, and the resulting filtrate was concentrated by ultrafiltration. The concentrated solution was 75% saturated with ammonium sulfate, and the resulting precipitates were collected and dissolved in 20 l of a 10 mM phosphate buffer solution (pH 7.0). This solution was desalted by ultrafiltration, and 2 kg of DEAE-cellulose previously equilibrated with a buffer of the same composition was added thereto. After washing DEAE-cellulose by use of 30 l of a buffer of the same composition, a buffer of the same composition containing 0.25 M sodium chloride was added, and the resulting eluate was desalted and concentrated by ultrafiltration. This solution was passed through a column packed with DEAE-Sepharose (produced by Pharmacia Fine Chemical Co.) previously equilibrated with a 10 mM phosphate buffer solution (pH 7.0). After washing the column with a buffer of the same composition containing 0.1 M sodium chloride, elution was carried out according to a linear concentration gradient method which increases the concentration of sodium chloride to 0.1 to 0.25 M. Lipase activities separated into three peaks (as shown in FIG. 5). Fractions showing the second activity peak were collected and subjected to salting-out with ammonium sulfate to collect precipitates formed in the range of from 55% saturation to 75% saturation. The precipitates were dissolved in a 10 mM phosphate buffer solution (pH 7.0), and the solution was desalted by ultrafiltration, followed by freeze-drying to obtain a purified lipase preparation. This purified preparation was subjected to column chromatography using hydroxy-apatite, and thereafter crystallized from an ammonium sulfate solution. Crystal form was diamond-shaped and plate-like.

The purified preparation obtained in the above had the specific activity of 9.2 U/mg protein, and was purified by about 130 times from the culture solution. Yield was about 17%.

REFERENCE EXAMPLE 1

The fractions of the first and the third activity peaks obtained by the DEAE-Sepharose column chromatography in Example 1 were further purified, respectively. The preparation obtained from the fraction of the first activity peak showed the property that it sufficiently acted on tributylin and weakly acted on methyl esters of fatty acids. The preparation obtained from the fraction of the third activity peak showed the property that it sufficiently acted on monoglycerides of fatty acids, but weakly acted on triglycerides of fatty acids. Such properties correspond to those of the lipases disclosed in the prior art set forth above.

EXAMPLE 2

The lipase obtained in Example 1, originating from the genus Penicillium was allowed to act on serum lipids to measure an amount of glycerol thus formed, whereby the reactivity of lipase to the lipids was observed.

There were mixed (i) 1.0 ml of a 0.1 M-PIPES buffer solution (pH 6.5) containing 0.5 U/ml of glycerol kinase, 4 U/ml of L-α-glycerophosphate oxidase, 2 U/ml of peroxidase, 3.3 mM of adenosine triphosphate, 0.5 mM of 4-aminoantipyrine, 2.0 mM of TOOS [N-ethyl-N-(2-hydroxy-3-sulfopropyl)-m-toluidine], 2 mM of magnesium chloride hexahydrate, 0.5 U/ml of lipase originating from the genus Penicillium, and polyethylene glycol p-isooctylphenyl ether (trademark: Triton X-100; produced by Rohm & Hass Co.) having a concentration ranging from 0.05 to 5.0%, and (ii) 0.01 ml of a standard serum sample (trademark: Lipid Serum II "EIKEN"; produced by Eiken Chemical Co., Ltd.), and the mixture was incubated at 37° C. for 10 minutes. The absorbance of the reaction mixture at 555 nm was measured to calculate the concentration of triglyceride in the sample (in terms of triolein). The concentrations of Triton X-100 used and the calculated values are shown in Table 2. It is seen that the activity of the lipase originating from the genus Penicillium is not inhibited even by the surface-active agent present in the concentration as high as 5%.

TABLE 2

| Concentration of Triton X-100 (%) | Triglyceride (mg/dl) |
| --- | --- |
| 0.05 | 284 |
| 0.1 | 282 |
| 0.5 | 287 |
| 1.0 | 287 |
| 5.0 | 285 |

EXAMPLE 3

There were mixed (i) 1.0 ml of a 0.1 M-PIPES buffer solution (pH 6.5) containing 0.5 U/ml of glycerol kinase, 4 U/ml of L-α-glycerophosphate oxidase, 2 U/ml of peroxidase, 3.3 mM of adenosine triphosphate, 0.5 mM of 4-aminoantipyrine, 2.0 mM of TOOS, 2 mM of magnesium chloride hexahydrate, and Triton X-100 having a concentration of 0.1 to 1.0%, and (ii) 0.02 ml of 25 U/ml of lipase originating from the genus Penicillium, and the mixture was incubated at 37° C. for 5 minutes. Subsequently, 0.01 ml of a serum sample was added, and the absorbance at 555 nm was measured with lapse of time.

Figure 6:
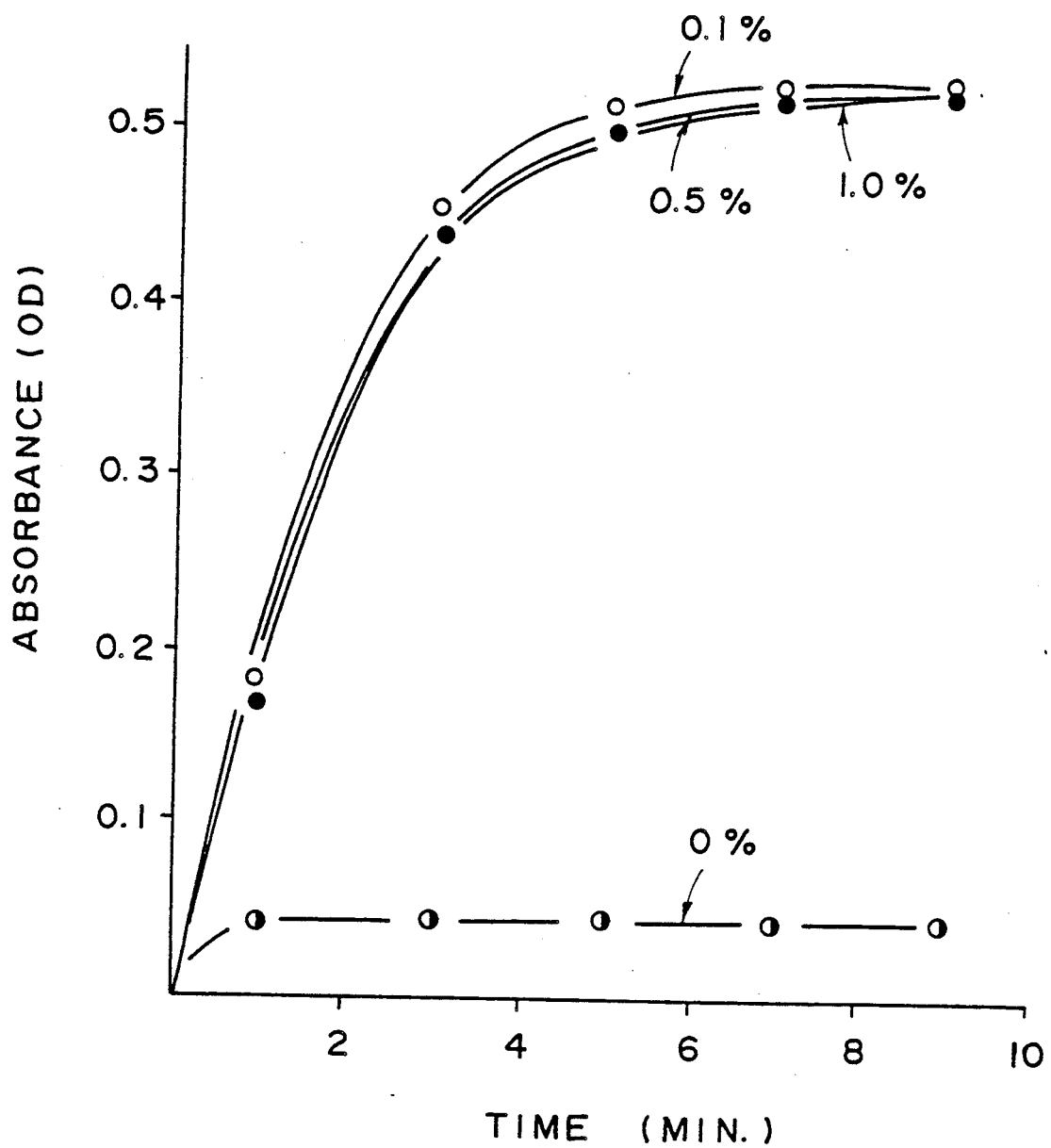
FIG. 6 is a graph showing the relationship between the concentration of Triton X-100 and the reactivity of the lipase of the present invention.

Relationship between the concentration of Triton X-100 and the reactivity of the lipase is shown in FIG. 6, from which it is seen that the lipase originating from the genus Penicillium is activated by Triton X-100, and its effect is little unchanged in the range of the concentration of 0.1 to 1.0%.

COMPARATIVE EXAMPLE 1

Glycerol formation activity and fatty acid formation activity of each lipase were measured to reveal that the present enzyme has a property that the glycerol formation activity is remarkably higher relative to the fatty acid formation activity as compared with commercially available lipases originating from the genus Pseudomonas (produced by Toyobo Co., Ltd. or by Amano Pharmaceutical Co., Ltd.) and those from the genus Chromobacterium (produced by Toyo Jozo Co., Ltd.).

TABLE 3

| Lipase | Activity (U/mg) | | $\frac{\text{Glycerol formation}}{\text{Fatty acid formation}} \times 100$ |
| --- | --- | --- | --- |
| | Glycerol Formation | Fatty acid Formation | |
| Present enzyme | 1.25 | 4.8 | 26 |
| From Pseudomonas, (Toyobo Co.) | 11.4 | 630 | 1.8 |
| From Pseudomonas, (Amano Pharm.) | 2.6 | 623 | 0.42 |
| From Chromobacterium, (Toyo Jozo Co.) | 4.5 | 564 | 0.80 |

COMPARATIVE EXAMPLE 2

Example 3 was repeated except that 50 U/ml, 100 U/ml, and 0.2 U/ml in nominal activity, respectively, of a commercially available lipase originating from the genus Pseudomonas (trademark: LPL "Amano" III; produced by Amano Pharmaceutical Co., Ltd.), lipase originating from Chromobacterium (produced by Toyo Jozo Co., Ltd.) or lipase originating from Pseudomonas (trademark: Lipoprotein Lipase Type A; Produced by Toyobo Co., Ltd.), was used in place of the lipase originating from the genus Penicillium.

Figure 7:
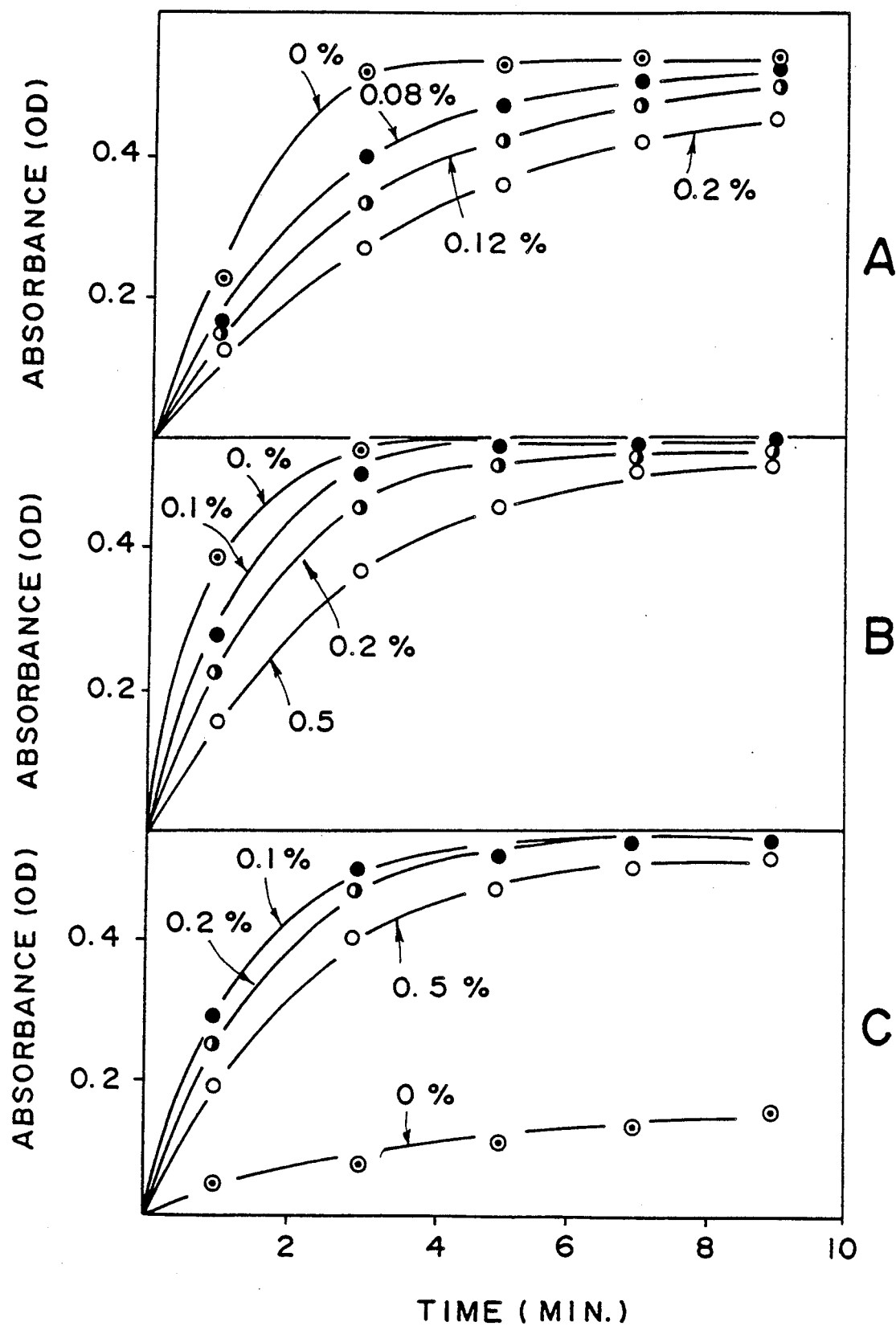
FIG. 7 is a graph showing the reactivities of respective lipases, wherein A refers to a lipase (LPL "Amano" III) originating from the genus Pseudomonas; B, a lipase originating from the genus Chromobacterium; and C, a lipase (lipoprotein lipase, Type A) originating from the genus Pseudomonas.

Relationship between the concentration of Triton X-100 and the reactivity of each lipase is shown in FIGS. 7-A to C. FIG. 7-A indicates a case where LPL "Amano" III was used; B, a lipase originating from Chromobacterium; and C, Lipoprotein Lipase-Type A. In all of these known lipases, the activities are seen to be inhibited as the concentration of Triton X-100 increases.

EXAMPLE 4

Example 3 was repeated except that 0.1 to 0.5% of a nonylphenol ethoxylate type surface-active agent (trademark: Adecatol NP-700; produced by Asahi Electro-Chemical Co., Ltd.) or 0.1 to 0.5% of a secondary straight chain alcohol ethoxylate type surface-active agent (trademark: Adecatol SO-135; produced by Asahi Electro-Chemical Co., Ltd.) was used in place of Triton X-100.

Figure 8:
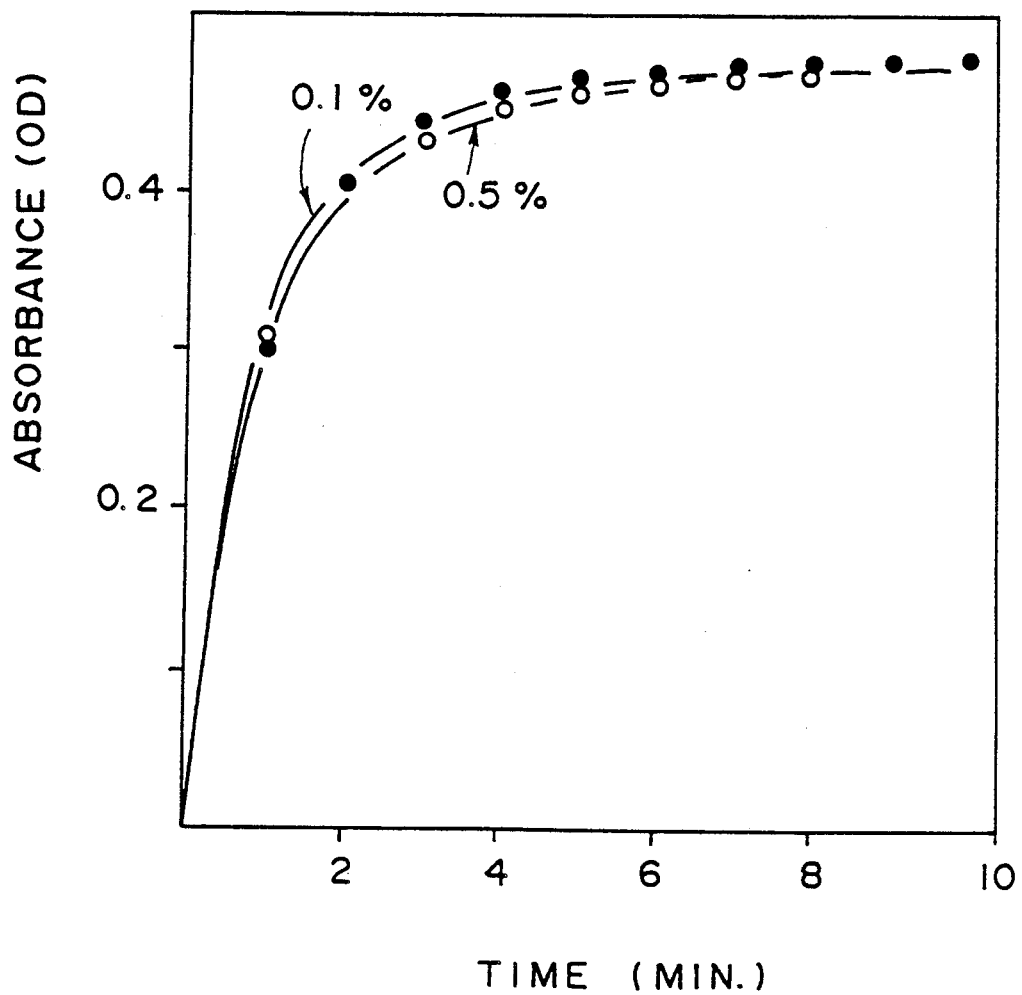
FIG. 8 is a graph showing the relationship between the concentration of a surface-active agent of nonylphenol ethoxylate type and the reactivity of the lipase of the present invention.
Figure 9:
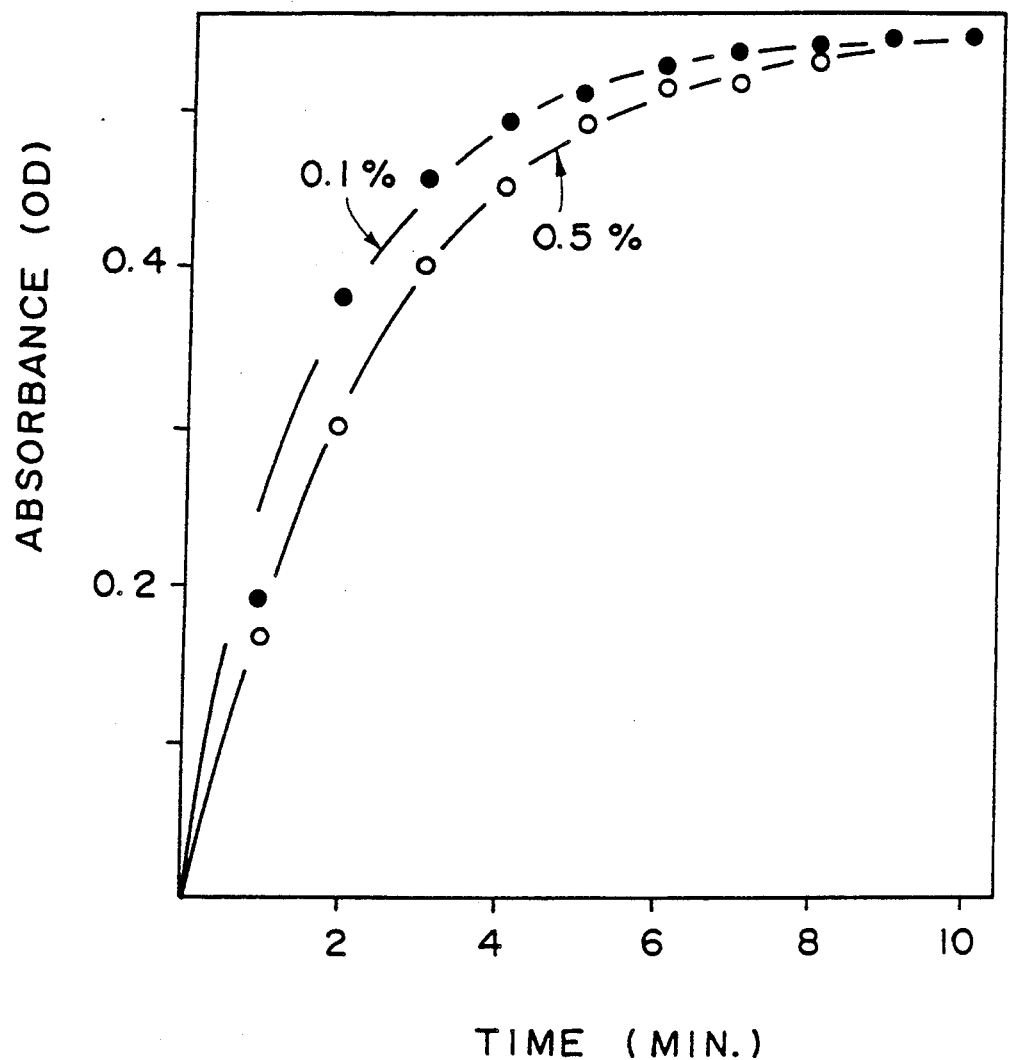
FIG. 9 is a graph showing the relationship between the concentration of a surface-active agent of secondary alcohol straight chain ethoxylate type and the reactivity of the lipase of the present invention.

Relationship between the concentration of surface-active agent and the reactivity of the lipase are shown in FIG. 8 and FIG. 9. FIG. 8 and FIG. 9 indicate cases where the nonylphenol ethoxylate type surface-active agent and the secondary straight chain alcohol type surface-active agent were used, respectively. Activities of the lipase originating from the genus Penicillium are seen to be substantially not inhibited by these surface-active agents.

According to the present invention, there is provided a novel lipase and a process for producing the same. The lipase of the present invention can substantially perfectly hydrolyze triglycerides in serum, and is substantially free from inhibition of activities even by a surface-active agent present in a high concentration.

According to the present invention, it is possible to substantially perfectly hydrolyze triglycerides without inhibition of activities by a surface-active agent, when a lipase originating from the genus Penicillium is acted on triglycerides in the presence of the surface-active agent. The present invention can be used for an assay of triglycerides in a biological body fluid.

What is claimed is:

1. Lipase isolated from *Penicillium cyclopium* characterized by the following properties:
   (1) Hydrolyzes triglycerides of fatty acids having 4–18 carbon atoms;
   (2) Hydrolysis of such triglycerides with such lipase produces at least 5 moles of glycerol per 100 moles of fatty acid;
   (3) Optimal pH range for said hydrolysis 5–7;
   (4) Stable in the pH range of 4.5–6;
   (5) Optimal temperature range for activity 35°–40° C.;
   (6) thermal stability up to about 35° C.;
   (7) Activated by surface-active agents, but not substantially inhibited by such surface-active agents in concentration up to 5%;
   (8) Molecular weight about 100,000 to 120,000;
   (9) Isoelectric point about pH 3.84.

2. Lipase according to claim 1, wherein said surface-active agent is an anionic surface-active agent.

3. Lipase according to claim 2, wherein said anionic surface-active agent is a polyethylene glycol alkyl ether.

4. A process for producing a lipase characterized by the following properties:
   (1) Hydrolyzes triglycerides of fatty acids having 4–18 carbon atoms;
   (2) Hydrolysis of such triglycerides with such lipase produces at least 5 moles of glycerol per 100 moles of fatty acid;
   (3) Optimal pH range for said hydrolysis 5–7;
   (4) Stable in the pH range of 4.5–6;
   (5) Optimal temperature range for activity 35°–40° C.;
   (6) Thermal stability up to about 35° C.;
   (7) Activated by surface-active agents, but not substantially inhibited by such surface-active agents in concentration up to 5%;
   (8) Molecular weight about 100,000 to 120,000;
   (9) Isoelectric point about pH 3.84;
   which comprises cultivating a strain belonging to *Penicillium cyclopium* capable of producing said lipase and collecting said lipase from the resulting culture.

5. The process for producing a lipase according to claim 4 from *Penicillium cyclopium* (ATCC 34613).

6. Method of assaying triglycerides which comprises reacting such triglyceride with a lipase isolated from *Penicillium cyclopium* and assaying glycerol liberated from the triglyceride, the lipase being characterized by the following properties:
   (1) Hydrolyzes triglycerides of fatty acids having 4–18 carbon atoms;
   (2) Hydrolysis of such triglycerides with such lipase produces at least 5 moles of glycerol per 100 moles of fatty acid;
   (3) Optimal pH range for said hydrolysis 5–7;
   (4) Stable in the pH range of 4.5–6;
   (5) Optimal temperature range for activity 35°–40° C.;
   (6) Thermal stability up to about 35° C.;
   (7) Activated by surface-active agents, but not substantially inhibited by such surface-active agents in concentration up to 5%;
   (8) Molecular weight about 100,000 to 120,000;
   (9) Isoelectric point about pH 3.84.

7. Method of assaying triglyceride according to claim 6, wherein said surface-active agent is an anionic surface-active agent.

8. Method of assaying triglyceride according to claim 7, wherein said anionic surface-active agent is a polyethylene glycol alkyl ether.

9. The method of claim 6 wherein the lipase is isolated from *Penicillium cyclopium* (ATCC 34613).

* * * * *